United States Patent
DiFoggio et al.

(10) Patent No.: US 7,694,734 B2
(45) Date of Patent: Apr. 13, 2010

(54) METHOD AND APPARATUS FOR INSULATING A RESONATOR DOWNHOLE

(75) Inventors: Rocco DiFoggio, Houston, TX (US); Christopher J. Powell, Houston, TX (US); Peter W. Reittinger, Katy, TX (US); Louis Perez, Jr., Houston, TX (US); Srdjan Stankovic, Houston, TX (US); Paul Bergren, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 233 days.

(21) Appl. No.: 11/262,644

(22) Filed: Oct. 31, 2005

(65) Prior Publication Data

US 2007/0095535 A1 May 3, 2007

(51) Int. Cl.
 *E21B 47/00* (2006.01)
(52) U.S. Cl. .................. 166/250.01; 73/152.58; 174/31.5
(58) Field of Classification Search ........... 166/250.01, 166/302; 702/6; 73/152.18, 152.55, 152.58; 324/326, 324; 439/278; 174/31.5
See application file for complete search history.

(56) References Cited

U.S. PATENT DOCUMENTS

| | | | | |
|---|---|---|---|---|
| 2,258,219 A * | 10/1941 | Rochow | ............... | 428/390 |
| 2,352,974 A * | 7/1944 | Rochow | ............... | 528/397 |
| 3,401,276 A * | 9/1968 | Curran et al. | ............... | 310/320 |
| 6,207,277 B1 * | 3/2001 | Shieh | ............... | 428/375 |
| 6,213,805 B1 * | 4/2001 | Jedlitschka et al. | ......... | 439/271 |
| 6,938,470 B2 | 9/2005 | DiFoggio et al. | | |
| 2001/0001224 A1 | 5/2001 | Ishikawa et al. | | |
| 2001/0004226 A1 | 6/2001 | Piazza et al. | | |
| 2001/0017505 A1 | 8/2001 | Aratake et al. | | |
| 2001/0022488 A1 | 9/2001 | Kawauchi et al. | | |
| 2001/0054860 A1 | 12/2001 | Knowles | | |
| 2002/0017830 A1 | 2/2002 | Ikeda et al. | | |
| 2002/0021059 A1 | 2/2002 | Knowles et al. | | |
| 2002/0096974 A1 | 7/2002 | Moon et al. | | |
| 2002/0113527 A1 | 8/2002 | Kawashima | | |
| 2002/0125794 A1 | 9/2002 | Tanaya et al. | | |
| 2002/0166379 A1 | 11/2002 | Paros et al. | | |
| 2002/0178787 A1 | 12/2002 | Matsiev et al. | | |
| 2002/0189061 A1 | 12/2002 | Kim et al. | | |
| 2003/0067248 A1 * | 4/2003 | Piazza et al. | ............... | 310/321 |
| 2003/0074036 A1 * | 4/2003 | Prutchi et al. | ............... | 607/60 |
| 2003/0080652 A1 | 5/2003 | Kawashima | | |
| 2003/0107302 A1 | 6/2003 | Birth et al. | | |
| 2003/0168943 A1 | 9/2003 | Matsuyama et al. | | |
| 2003/0168944 A1 | 9/2003 | Shimizu et al. | | |
| 2003/0168947 A1 | 9/2003 | Kawashima | | |
| 2004/0007065 A1 | 1/2004 | Fujimoto et al. | | |
| 2004/0085004 A1 | 5/2004 | Chiba et al. | | |
| 2004/0095046 A1 | 5/2004 | Ouchi et al. | | |
| 2004/0155561 A1 | 8/2004 | Tanaya et al. | | |

(Continued)

*Primary Examiner*—Daniel P Stepheson
(74) *Attorney, Agent, or Firm*—G. Michael Roebuck

(57) ABSTRACT

A method and apparatus are provided for insulating electrical connections to a resonator from fluid downhole under extreme pressure and temperature conditions downhole. The method and apparatus provide a pliable insulator that maintains electrical isolation between a resonator electrical connection during exposure to high pressures downhole. The insulator is substantially chemically non reactive so that the insulator maintains electrical isolation between the resonator electrical connections during exposure to fluids downhole. The insulator has a thermal coefficient of expansion in a range so that the insulator maintains electrical isolation between the resonator electrical connections during exposure to high temperatures downhole.

21 Claims, 3 Drawing Sheets

U.S. PATENT DOCUMENTS

| | | |
|---|---|---|
| 2004/0194534 A1 | 10/2004 | Porter et al. |
| 2004/0236512 A1* | 11/2004 | DiFoggio et al. ............... 702/6 |
| 2004/0244487 A1 | 12/2004 | Kolosov et al. |
| 2004/0250622 A1 | 12/2004 | Kolosov et al. |
| 2005/0005676 A1 | 1/2005 | Crawley et al. |
| 2005/0017604 A1 | 1/2005 | Yamada |
| 2005/0040737 A1 | 2/2005 | Tanaya |
| 2005/0062368 A1 | 3/2005 | Hirasawa et al. |
| 2005/0116587 A1 | 6/2005 | Ono et al. |
| 2005/0122006 A1 | 6/2005 | Matsudo et al. |
| 2005/0134150 A1 | 6/2005 | Kikushima et al. |
| 2005/0134154 A1 | 6/2005 | Kawashima |
| 2005/0140252 A1 | 6/2005 | Miyata et al. |
| 2005/0184628 A1 | 8/2005 | Kawashima |
| 2005/0206277 A1 | 9/2005 | Eguchi et al. |
| 2005/0262944 A1* | 12/2005 | Bennett et al. ............... 73/592 |
| 2005/0264140 A1 | 12/2005 | Miyazaki |
| 2005/0270113 A1 | 12/2005 | Kawashima |
| 2005/0285483 A1 | 12/2005 | Satoh et al. |
| 2006/0066185 A1 | 3/2006 | Tanaya |
| 2006/0070220 A1 | 4/2006 | Kawashima |
| 2006/0082261 A1 | 4/2006 | Tanaya |

* cited by examiner

METHOD AND APPARATUS FOR INSULATING A RESONATOR DOWNHOLE

BACKGROUND OF THE INVENTION

1. Field of the Invention

The present invention relates to the field of downhole fluid analysis in hydrocarbon producing wells for determining fluid density, viscosity, and other parameters for a fluid downhole in a borehole during monitoring while drilling or wire line operations. More particularly, the present invention relates to a method and apparatus for insulating electrical connections to a resonator from conductive fluid downhole.

2. Background Information

U.S. Pat. No. 6,938,470 by DiFoggio et al. describes a downhole method and apparatus for using a mechanical resonator, for example, a tuning fork to provide real-time direct measurements and estimates of the viscosity, density and dielectric constant of formation fluid or filtrate in a hydrocarbon producing well. As shown generally in DiFoggio et al. (U.S. Pat. No. 6,938,470), a resonator, such as a piezoelectric tuning fork is placed downhole as an addition to a fluid analyzer module.

One obstacle to the successful use of resonators such as tuning forks downhole has been electrical shorting of resonator electrical connections when exposed to conductive fluids downhole. Downhole fluids are under the extreme pressure and temperature encountered downhole. Downhole pressure can exceed 30,000 pounds per square inch (PSI) and temperature can exceed 350° F. Fluid downhole under high pressure and temperature can force downhole fluid into the electrical insulation around a resonator and short out the electrical connections to the resonator.

SUMMARY OF THE INVENTION

The present invention provides a method and apparatus for insulating resonator electrical connections from fluid under extreme pressure and temperature conditions downhole. The apparatus of present invention provides a pliable insulator that maintains electrical isolation between the resonator electrical connections during exposure to high pressures downhole. The insulator is substantially chemically non reactive so that the insulator maintains electrical isolation between the resonator electrical connections during exposure to corrosive or solvating fluids downhole. The insulator has a thermal coefficient of expansion in a range so that the insulator maintains electrical isolation between the resonator electrical connections during exposure to high temperatures downhole.

In one aspect of the invention an apparatus is provided for insulating a resonator downhole. The apparatus contains a resonator for interacting with a fluid downhole, an electrical connection to the resonator and a pliable insulator for insulating the electrical connection from the fluid. The insulator maintains electrical isolation between the electrical connection and the fluid when exposed to downhole pressure. In another aspect of the invention the insulator maintains electrical isolation between the electrical connection and the fluid when exposed to downhole temperature. In another aspect of the invention the insulator remains at a substantially constant volume when exposed to the fluid downhole, although the insulator's shape may change.

In another aspect of the invention a method is provided for insulating a resonator downhole. The method provides steps for placing a resonator in fluid communication with a fluid downhole and insulating an electrical connection to the resonator from the fluid using a pliable insulator. The method further provides for maintaining electrical isolation between the electrical connection and the fluid while exposing the resonator to downhole pressure. In another aspect of the invention the method provides for maintaining electrical isolation further comprises maintaining electrical isolation between the electrical connection and the fluid while exposing the insulator to downhole temperature. In another aspect of the invention the method provides for maintaining the insulator at a substantially constant volume when exposed to the fluid downhole.

Examples of certain features of the invention have been summarized here rather broadly in order that the detailed description thereof that follows may be better understood and in order that the contributions they represent to the art may be appreciated. There are, of course, additional features of the invention that will be described hereinafter.

BRIEF DESCRIPTION OF THE FIGURES

For a detailed understanding of the present invention, references should be made to the following detailed description of the exemplary embodiment, taken in conjunction with the accompanying drawings, in which like elements have been given like numerals, wherein.

DETAILED DESCRIPTION OF THE INVENTION

Figure 1:
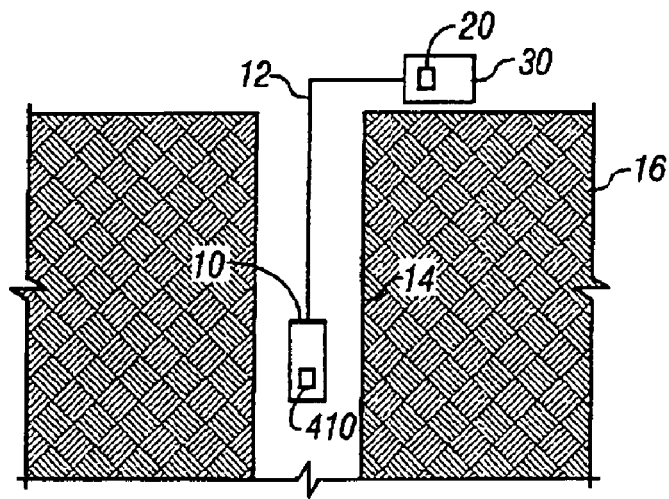
FIG. 1 is a schematic diagram of an embodiment of the present invention deployed on a wireline in a downhole environment.

The present invention provides a method and apparatus for insulating a resonator that is used for estimating a property of a fluid downhole. The method and apparatus provide a suitable insulator to electrically insulate electrical connections to the resonator. In the present example of the invention the resonator is shown as a piezoelectric tuning fork. The resonator, however, can be any resonator suitable for use downhole, including but not limited to a thickness shear mode (TSM) resonator, a mechanical resonator, a bar bender resonator, a disk bender resonator, a cantilever, a micro-machined membrane or a torsion resonator. The present invention provides a method and apparatus for insulating the resonator to provide electrical isolation to prevent the tuning fork electrical connections from being shorted out by conductive fluid downhole. Conductive fluid may be formation water or brine. Under downhole pressures exceed 30,000 PSI and 350 degrees Fahrenheit, conductive fluid can be forced into the electrical insulation around a resonator insulator and electrically short out the resonator electrical connections and this conductive fluid can remain in the insulator even after the assembly has been flushed with crude oil.

The present invention provides insulation that isolates the resonator electrical connection from any conductive fluid downhole. The present invention provides an insulator that is made of a pliable material that does not crack under exposure to hydrostatic pressure from downhole fluid. In the past, rigid epoxy insulators and some silicone insulators have failed downhole. One problem with rigid epoxy insulators is that any slight movement of the insulator covering the electrical connections and bare-wire electrical leads of the resonator or tuning fork relative to the tuning fork (which is made of piezoelectric material, for example lithiumniobate) can create a leakage path for conductive fluid to invade and short out the resonator electrical connections downhole. In particular, shorting of electrical connections to the electrodes of a piezoelectric tuning fork has been observed and attributed to the rigid insulators developing microcracks under downhole pressure cycling as the insulator travels downhole and returns to the surface. Rigid insulators may also separate from the resonator due to thermal expansion when exposed to extreme downhole temperatures. Rigid insulators have also been observed to attenuate a signal from a piezoelectric tuning fork by a factor of five. It is believed that the rigid insulator dampens the vibration of a central member connecting the tines of a tuning fork and in so doing dampens the vibration of the tines of the tuning fork. A pliable insulator of ordinary silicone rubber lacks the chemical resistance to the many solvents present in crude oil so it can swell and peel away from the tuning fork opening up pathways for conductive fluids to leak in and short out the tuning fork. A fluorosilicone rubber has both pliability and chemical resistance.

Typically the resonator, i.e., a tuning fork is placed into a fluid in a fluid flow path. In practice, that fluid can alternate between slugs of brine and crude oil during pumping. In immersing and monitoring the turning fork in a fluid, such as formation hydrocarbons or brine, properties of that fluid can be estimated. Electrical communication with the resonator is established by attaching electrical leads to the resonator electrical connections. In the present example, electrical leads are attached to electrical connections which connect to electrodes in the tuning fork. The insulator electrically isolates the electrical connections to the electrodes from the conductive fluid.

In one embodiment of the invention, the tuning fork electrical leads pass through a high pressure feed through which penetrates a wall of the fluid flow path. The turning fork is disposed in the conductive fluid in the flow path. The electrical leads provide electrical communication between electrodes inside of the tuning fork and electronics located inside or outside of the flow path. In the present example, electronics contain a controller and monitoring equipment and are placed outside of the flow path. The electrical leads are run through the high pressure feed through to establish electrical communication with the electronics so that the resonator or tuning fork can be controlled and monitored by the electronics through the electrical connections.

Any movement of the resonator, (i.e., the piezoelectric tuning fork) or the electrical leads relative to the high pressure feed through can create a void in the bond between a rigid epoxy insulator, the high pressure feedthrough, and the resonator (tuning fork). The resonator can be made of thin metal electrodes on a glass or ceramic piezoelectric substrate material. The high pressure feedthrough can be made of glass with metal pins through the glass, which bond to the glass or of metal pins through high-temperature engineering plastics such as polyetheretherketone (PEEK), or polyetherketone (PEK). Pressure cycling can also cause the rigid epoxy insulator to develop micro cracks allowing conductive fluid to leak in. Any crack or breach in a bond between the rigid insulator and the resonator electrical leads or electrodes can allow high pressure conductive fluid to leak through the crack and electrically short out the electrical connections to the electrodes thereby rendering the tuning fork useless. Electrical shorts can disable the tuning fork so that the analysis capability of the turning fork is lost to the downhole sample analysis effort.

Relative movements between the rigid epoxy insulator can occur because the materials from which the rigid insulator, tuning fork and high pressure feed through are made may possess different coefficients of thermal expansion or compressibility (reciprocal bulk modulus) with pressure. These relative movements can create a leakage path such as a void or crack through which conductive downhole fluid can travel. Relative movement can occur when the tuning fork, rigid epoxy and high pressure feed through are exposed to extreme downhole temperatures exceeding 200-375 degrees Fahrenheit. Such temperatures represent radical temperature cycling changes from the surface temperatures of 0-100 degrees Fahrenheit.

The materials from which the tuning fork, high pressure feed through and rigid epoxy are made may also each possess a different bulk modulus. The bulk modulus K gives the change in volume V of a solid substance as the pressure P on it is changed, $$K = -V(dP/dV) = \rho(\partial P/\partial \rho)$$

where $\rho$ is the density. The bulk modulus has units of pressure.

This variance in the bulk modulus of the materials from which the tuning fork, high pressure feed through and rigid epoxy insulator are made present a problem when pressure changes are encountered. The tuning fork, rigid epoxy insulator and high pressure feed through are each made of a different material each having a different bulk modulus. Thus the volumes of the turning fork, rigid epoxy insulator and high pressure feed through change at different rates when exposed to the same pressure differential, thereby creating a void between the tuning fork, high pressure feed through and rigid epoxy insulator. This void can be used as a flow path for high pressure conductive downhole fluid.

The resonator/tuning fork, rigid epoxy insulator and high pressure feed through are exposed to pressure changes ranging from 15 PSI at the surface to 10,000-30,000 PSI downhole. During high pressure cycling, cracks can be formed in the rigid epoxy insulator. Cracks can be formed when the tuning fork, rigid epoxy and feed through are exposed to extreme downhole pressures exceeding 30,000 PSI and returned to relatively low pressure at the surface.

This pressure cycling can cause problems in using the tuning fork downhole due to cracking of the rigid insulator after pressure cycling. Pressure cycle cracking has been experienced when using a rigid epoxy insulator such as a Mereco epoxy by itself. The rigid Mereco insulator material may be used successfully in conjunction with a pliable insulator as discussed below. Mereco is tradename of a portfolio of specialty chemicals consisting of formulated epoxy, urethane, silicone, and ultraviolet (UV) curing compounds produced by Mereco Technologies Group Companies, West Warwick, R.I.

Based on experiments to date, a suitable insulator material for downhole use is a pliable, chemically-resistant insulator material that maintains electrical isolation between the electrical connections to the resonator and any conductive fluid at downhole temperature and pressure. In the present application the term pliable is intended to mean capable of being bent or flexed or twisted without breaking or capable of being shaped, bent or drawn out without breaking, cracking, tearing or creating a void in the material.

The pliable material includes but is not limited to elastomers, which are polymers that can be stretched or compressed yet rebound to their original length when released. The insulator should not overly dampen oscillation of a resonator or attenuate a signal from a resonator as a highly viscous fluid will also dampen and attenuate a resonator vibration and a signal from the resonator. Based on current observations it appears that a class of elastomers including but not limited to halogenated elastomers is suitable for use as an insulator material in the present invention. International Standards Organization (ISO) recommended abbreviations for these compounds and a few trade names are listed below. The halogenated elastomers include but are not limited to standard fluoroelastomers (FKM, such as DUPONT's Viton), fluorosilicones (MQ, VMQ, PMQ, FMQ such as NUSIL's CF1-3510 or DOW CORNING's Silastic), perfluoroelastomers (FFKM such as DUPONT's Kalrez), and tetra-fluoroethylene/propylene (FEPM such as Asahi Glass Company's AFLAS).

One suitable pliable insulator material, which has performed satisfactorily in experimental use as an insulator material, is a fluorosilicone elastomer available commercially as NUSILN CF1-3510 from Nusil Technology, 1050 Cindy Lane, Capinteria, Calif. 93013. In an experimental test, the NUSIL CF1-3510 fluorosilicone elastomer did not crack under downhole pressure and temperature cycling. The NUSIL fluorosilicone elastomer is also substantially chemically non reactive so that it does not swell when exposed to crude oil or peel away from the resonator surface to which it is attached. Another suitable elastomer appears to be DOW CORNING 5-8601 fluorosilicone LSR. It appears that an elastomer having a durometer value of less than 50 and tensile PSI of 500 or greater is suitable for use as an insulator in the present invention, when the elastomer does not react adversely with formation fluid downhole to create a void in the insulator.

An elastomer such as the NUSIL fluorosilicone elastomer is facilitated for use in the present invention downhole when used in conjunction with a primer used as an adhesion facilitator. A primer is an undercoat applied to prepare surface, as for enhancing adhesion between two surfaces. Numerous suitable primers are available commercially. One suitable primer that has been successful in an experimental test is CF6-135 primer, available commercially from NUSIL. The adhesion facilitating primer improves adhesion to hard-to-bond surfaces such as glass-like lithium niobate from which the piezoelectric tuning fork can be made. Since the insulator bonds to the high pressure feed through and the tuning fork, any void in the insulator bond between the high pressure feed through and the tuning fork may create a leakage path for conductive fluid to short out the tuning fork electrical connections.

Unlike a rigid epoxy, which can crack under such extreme pressure cycling, the fluorosilicone elastomer is suitable for use as an insulator for the tuning fork downhole. The flexible fluorosilicone elastomer does not crack under pressure cycling. However, fluorosilicone elastomer is also substantially chemically non reactive. Unlike ordinary silicone, a halogenated silicone, such as the fluorosilicone elastomer, the volume remains substantially constant and does not substantially swell when soaked in formation fluid (i.e., crude oil) during sampling operations downhole. The volume of some plain silicones can change or swell sufficiently to peel away from the fork providing a path through which high pressure downhole fluid can leak and short out the electrodes of the tuning fork.

The CF6-135 primer does not require roughening of the tuning fork surface to effectively facilitate the bond between the fluoro silicone elastomer and the tuning fork. Many other primers can be used after roughening or scarification of the tuning fork surface to prevent the cured fluorosilicone elastomer from being easily peeled away from the tuning fork surface.

The fluorosilicone elastomer is pliable so that it allows substantially free movement of the resonator or tuning fork to which it is applied as an insulator. It has been observed that rigid epoxy dampens the resonance of the tuning fork. Damping of resonance by a factor of five has been observed in association with the use of a rigid epoxy insulator in conjunction with a piezoelectric resonator. A dampening of more than 20-50% as experienced when using the rigid insulator with the tuning fork is considered undesirable, depending on the application. Highly viscous fluids will also dampen a tuning fork so tolerance to cumulative damping by the insulator and fluid depend on the application and the viscosity of the fluid in which the tuning fork is used. In an alternative embodiment the resonator can be sand blasted or mechanically scarified, chemically scarified or laser etched to promote adhesion.

Thus, a characteristic of a suitable insulator material for use with the present invention is that the insulator material is chemically resistant so that the volume of the insulator remains substantially constant when exposed to formation fluid. Another characteristic of a suitable insulator material for use with the present invention is that the insulator does not crack or create an opening between the high pressure feed through, tuning fork and insulator when submitted to pressure cycling. Another characteristic of a suitable insulator material for use with the present invention is that the insulator does not create a void between the high pressure feed through, tuning fork and insulator when submitted to pressure cycling due to a different bulk modulus for the insulator, turning fork and high pressure feed through. Another characteristic of a suitable insulator material for use with the present invention is that the insulator does not create a void between the high pressure feed through, tuning fork and insulator when submitted to temperature cycling due to a different thermal expansion coefficient for the insulator, turning fork and high pressure feed through.

In another embodiment of the invention, the insulator can be made as a two- or three-layer structure (a "sandwich") of alternating an elastomeric insulator (such as the Nusil fluoroelastomer discussed above) and a rigid encapsulant (such as the Mereco epoxy discussed above) to provide additional mechanical support to the tuning fork. The additional support exceeds that provided by the fluoroelastomeric insulator alone.

Turning now to FIG. 1, FIG. 1 is a schematic diagram of an embodiment of the present invention deployed on a wire line in a downhole environment. FIG. 1 is a schematic diagram of an embodiment of the present invention deployed on a wire line in a downhole environment. As shown in FIG. 1, a downhole tool 10 containing a mechanical resonator 410 is deployed in a borehole 14. The borehole is formed in formation 16. Tool 10 is deployed via a wireline 12. Data from the tool 10 is communicated to the surface to a computer processor 20 with memory inside of an intelligent completion system 30.

Figure 2:
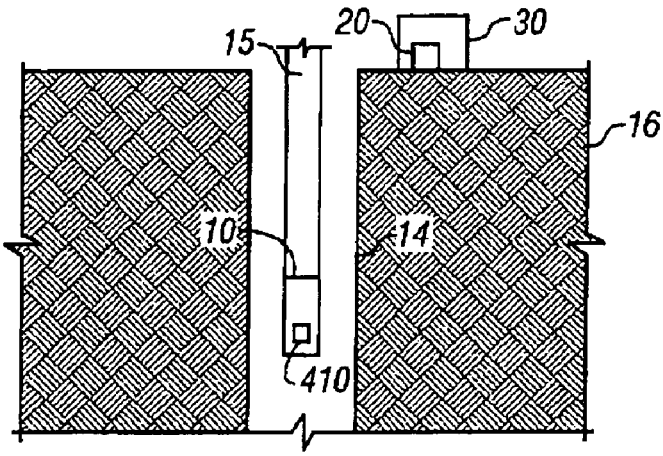
FIG. 2 is a schematic diagram of an embodiment of the present invention deployed on a drill string in a monitoring while drilling environment.
Figure 3:
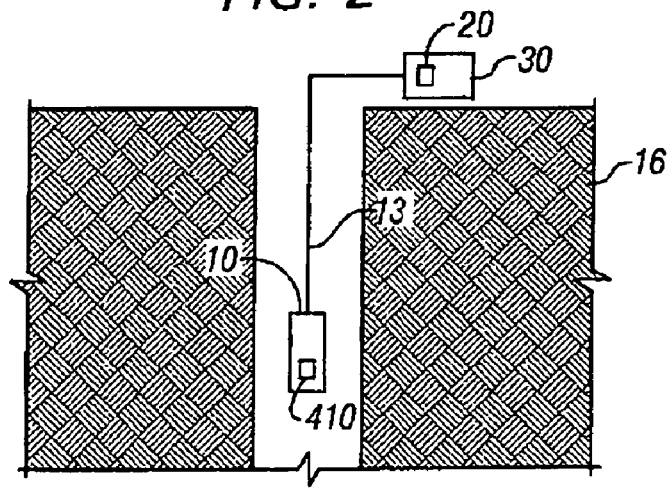
FIG. 3 is a schematic diagram of an embodiment of the present invention deployed on a flexible tubing in a downhole environment.

FIG. 2 is a schematic diagram of an embodiment of the present invention deployed on a drill string 15 in a monitoring while drilling environment. FIG. 3 is a schematic diagram of an embodiment of the present invention deployed on a flexible tubing 13 in a downhole environment.

Figure 4:
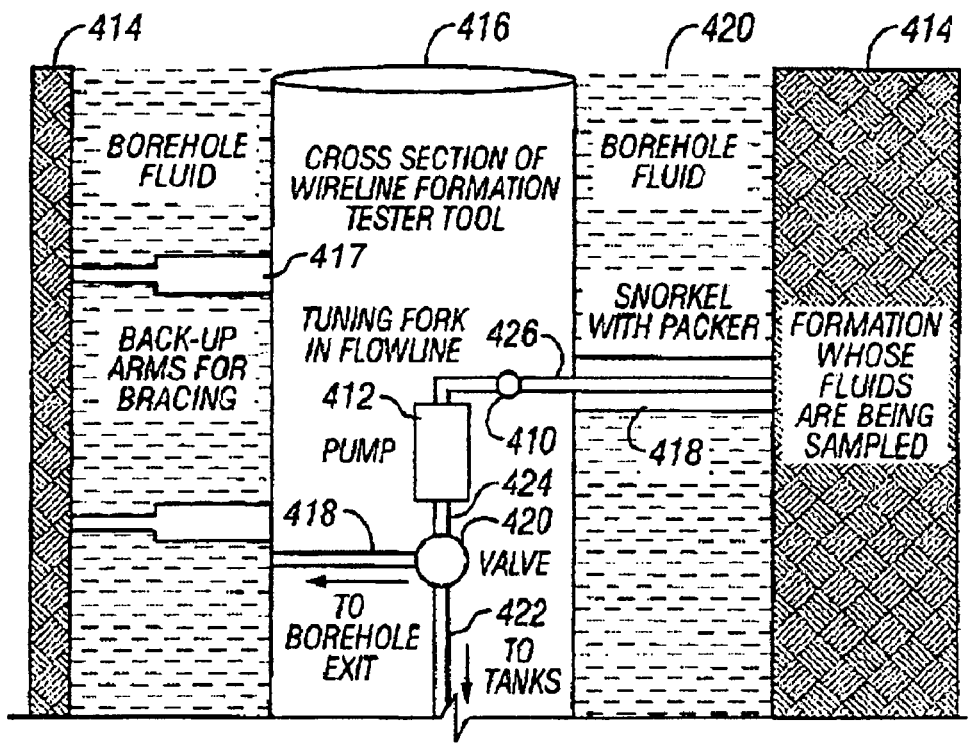
FIG. 4 is a schematic diagram of an embodiment of the present invention as deployed in a wireline downhole environment showing a cross section of a formation tester tool.

FIG. 4 is a schematic diagram of an embodiment of the present invention as deployed in a wireline downhole environment showing a cross section of a wireline formation tester tool. As shown in FIG. 4, tool 416 is deployed in a borehole 420 filled with borehole fluid. The tool 416 is positioned in the borehole by backup support arms 417. A packer with a snorkel 418 contacts the borehole wall for extracting formation fluid from the formation 414. Tool 416 contains tuning fork 410 disposed in flowline 426. Any type of flexural mechanical oscillator or thickness shear mode resonator is suitable for downhole deployment in fluid in the tool of the present invention. The mechanical oscillator, shown in FIG. 4 as a tuning fork is excited by an electrical current applied to a set of tuning fork electrodes. The tuning fork is monitored to determine density, viscosity and, depending on its construction, the dielectric coefficient of the formation fluid. The electronics for exciting and monitoring the flexural mechanical resonator are housed in the tool 10. Pump 412 pumps formation fluid from formation 414 into flowline 426. Formation fluid travels through flow line 424 in into valve 420 which directs the formation fluid to line 422 to save the fluid in sample tanks or to line 418 where the formation fluid exits to the borehole. The tuning fork is excited and its response in the presence of a formation fluid or water is utilized to determine fluid density, viscosity and, depending on its construction, on the dielectric coefficient while the fluid is being pumped by pump 412 or while the fluid is static, that is, when the pump 412 is stopped.

Figure 5:
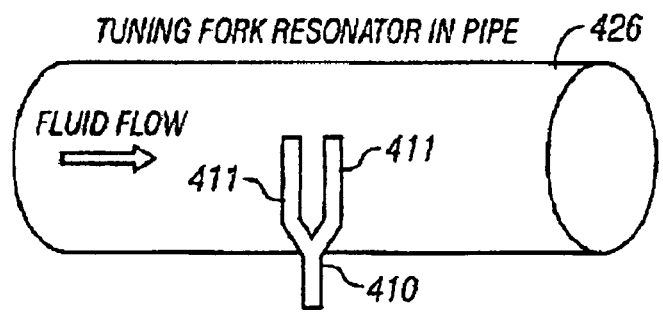
FIG. 5 is a schematic diagram of an embodiment of the present invention illustrating a tuning fork deployed in a fluid flow path.
Figure 6:
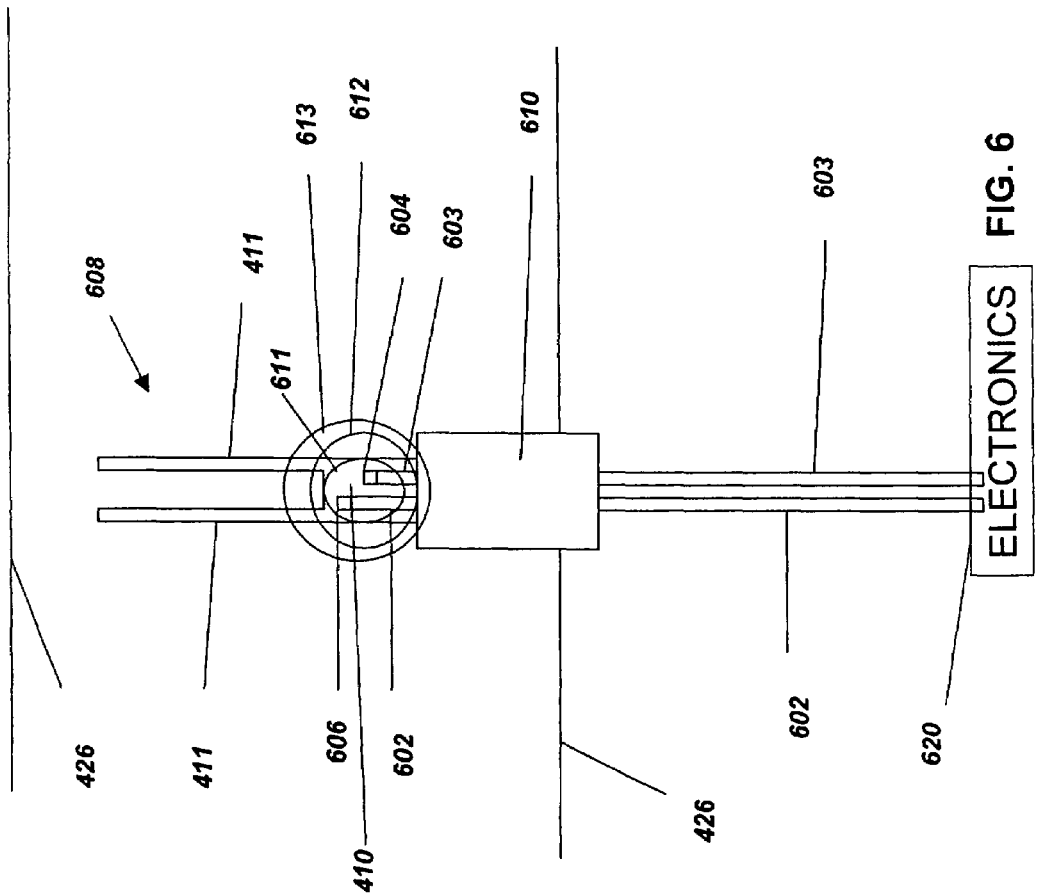
FIG. 6 is a schematic diagram of an embodiment of the present invention illustrating the tuning fork deployed in a fluid flow pipe illustrating an insulator covering for an electrical connection to the tuning fork in the fluid flow path.

Turning now to FIG. 5, FIG. 5 is a schematic diagram of an embodiment of the present invention illustrating a tuning fork deployed in a fluid flow path 426. Tuning fork tines 411 extend from tuning fork center member 410 into fluid flow path 426. FIG. 6 illustrates an insulator 612 covering for an electrical connection to the tuning fork disposed in the fluid flow path. As shown in FIG. 6, electrical leads 602 and 603 run through a high pressure feed through 610. The electrical leads 602 and 603 attach to turning fork electrical connections 604 and 606. Electrical connections 604 and 606 attach to electrodes inside of turning fork 608. The insulator 612 is provided to cover the bare electrical leads 602 and 603 and electrical connections 604 and 606. Insulator 612 deforms rather than cracks under downhole pressure so that the does not crack under pressure cycling and allow brine or formation fluids to penetrate the cracks or short out the electrical connections or leads under the insulator.

The insulator 612 covers the tuning fork electrical connections 604, 606 to the tuning fork electrodes to the extent necessary to prevent electrical shorting of the electrical connections 604, 606 from conductive fluid. The conductive fluid can be water, formation fluid or some other conductive fluid. The insulator is also chemically resistant so that the volume of the insulator does not change significantly when exposed to formation fluid. An adhesion promoter such as a CF6-135 primer 611 can be placed on the tuning fork before applying insulator 612 to facilitate adhesion of the insulator to the tuning fork. A rigid epoxy 613 can be placed over the insulator 612 or under the insulator 612 to strengthen the insulator 612. As discussed above, the insulator is pliable so that the vibration of the tuning fork tines 411 is substantially unencumbered.

While the foregoing disclosure is directed to the exemplary embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated.

The invention claimed is:

1. An apparatus for insulating a resonator downhole comprising:
   a resonator having a fixed end attached to an electrical connection and a free vibrating end in physical contract with only a fluid for interacting with the fluid downhole; and
   a pliable insulator the covering only the fixed end of the resonator and the electrical connection for insulating the electrical connection from the fluid downhole, wherein the insulator does not crack so that the insulator maintains electrical isolation between the electrical connection and the fluid when exposed to downhole pressure.

2. The apparatus of claim 1, wherein the insulator has a thermal coefficient of expansion so that it maintains electrical isolation between the electrical connection and the fluid when exposed to downhole temperature.

3. The apparatus of claim 2, wherein the insulator maintains electrical isolation between the electrical connection and the fluid when exposed to over 300 degrees Fahrenheit downhole.

4. The apparatus of claim 1, wherein the insulator is substantially chemically non reactive so that the insulator remains at a substantially constant volume when exposed to the fluid downhole.

5. The apparatus of claim 4, wherein the insulator comprises a halogenated elastomer.

6. The apparatus of claim 5, wherein the halogenated elastomer is a silicone selected from a set consisting of a fluorinated silicone, chlorinated silicone, brominated silicone, iodinated silicone and astatinated silicone.

7. The apparatus of claim 1, further comprising:
   a high pressure feed through containing wires connecting the electrical connections to electronics, wherein the insulator has a bulk modulus sufficient to maintain electrical isolation between the wires and the fluid.

8. The apparatus of claim 1, wherein the insulator has a durometer value of less than 50 and a tensile PSI value greater than or equal to 500 so that the insulator attenuates a signal from vibration of the free end of the resonator in the fluid by less than fifty percent.

9. The apparatus of claim 1, further comprising:
   a rigid material covering the insulator to strengthen the insulator.

10. The apparatus of claim 1, further comprising:
    a primer placed between the resonator and the insulator to facilitate adhesion between the resonator and the insulator.

11. The apparatus of claim 10 wherein the primer is deformable.

12. The apparatus of claim 1, wherein the resonator is a flexural piezoelectric resonator.

13. A method for insulating a resonator downhole comprising:
    placing a resonator having a fixed end attached to the electrical connections and a free end in physical contact with only a fluid in fluid communication with the fluid downhole;
    insulating only the fixed end and the electrical connection to the resonator from the fluid downhole with a pliable insulator; and
    maintaining integrity of the insulator without cracking to provide continuous electrical isolation between the electrical connection and the fluid while exposing the resonator to downhole pressure.

14. The method of claim 13, wherein maintaining a volume of the insulator to provide continuous electrical isolation further comprises maintaining electrical isolation between the electrical connection and the fluid while exposing the insulator to downhole temperature.

15. The method of claim 13, wherein continuous electrical isolation between the electrical connection and the fluid further comprises maintaining the insulator at a substantially constant volume when exposed to the fluid downhole.

16. The method of claim 13, wherein the insulator comprises a halogenated elastomer selected from a set consisting of a fluorinated silicone, chlorinated silicone, brominated silicone, iodinated silicone and astatinated silicone.

17. The method of claim 13, wherein insulating further comprises insulating a high pressure feed though containing wires connecting electrical connections to electronics, wherein the insulator maintains a bond between the insulator and the feed though to provide continuous electrical isolation between the wires and the fluid.

18. The method of claim 13, wherein the insulator attenuates a vibration from the free end of the resonator by less than fifty percent.

19. The method of claim 13, further comprising:
covering the insulator with a rigid material.

20. The method of claim 13, further comprising:
priming the resonator to enhance adhesion between the resonator and the pliable insulator.

21. The apparatus of claim 1, wherein the insulator is pliable.

* * * * *